(12) United States Patent
Nardelli Haefliger et al.

(10) Patent No.: US 9,795,641 B2
(45) Date of Patent: Oct. 24, 2017

(54) ***SALMONELLA* STRAINS FOR USE IN THE TREATMENT AND/OR PREVENTION OF CANCER**

(71) Applicant: Centre Hospitalier Universitaire Vaudois (C.H.U.V.), Lausanne (CH)

(72) Inventors: Denise Nardelli Haefliger, Lausanne (CH); Patrice Jichlinski, Le Mont-sur-Lausanne (CH); Sonia Domingos Pereira, Epalinges (CH)

(73) Assignee: CENTRE HOSPITALIER UNIVERSITAIRE VAUDOIS (C.H.U.V.), Lausanne (CH)

( * ) Notice: Subject to any disclaimer, the term of this patent is extended or adjusted under 35 U.S.C. 154(b) by 0 days.

(21) Appl. No.: 14/888,831

(22) PCT Filed: May 7, 2014

(86) PCT No.: PCT/EP2014/059392
§ 371 (c)(1),
(2) Date: Nov. 3, 2015

(87) PCT Pub. No.: WO2014/180929
PCT Pub. Date: Nov. 13, 2014

(65) Prior Publication Data
US 2016/0074441 A1 Mar. 17, 2016

(30) Foreign Application Priority Data
May 7, 2013 (EP) .................................... 13166851

(51) Int. Cl.
| A61K 35/74 | (2015.01) |
| A61K 9/00 | (2006.01) |
| A61K 45/06 | (2006.01) |
| A61N 5/10 | (2006.01) |

(52) U.S. Cl.
CPC ............ *A61K 35/74* (2013.01); *A61K 9/0034* (2013.01); *A61K 45/06* (2013.01); *A61N 5/10* (2013.01)

(58) Field of Classification Search
CPC .............................. A61K 35/74; A61K 9/0034
See application file for complete search history.

(56) References Cited

U.S. PATENT DOCUMENTS

| 6,037,332 A | 3/2000 | Oladele et al. |
| 6,962,696 B1 | 11/2005 | Bermudes et al. |
| 2007/0298012 A1 | 12/2007 | King et al. |

FOREIGN PATENT DOCUMENTS

| EP | 1928492 B1 * | 8/2006 | ............. A61K 39/00 |
| EP | 2085466 A1 | 8/2009 | |
| WO | WO-98/15631 A1 | 4/1998 | |
| WO | WO-03/031599 A2 | 4/2003 | |
| WO | WO-03/063593 A1 | 8/2003 | |
| WO | WO-2005/123762 A2 | 12/2005 | |
| WO | WO-2006/076678 A2 | 7/2006 | |
| WO | WO-2008/091375 A2 | 7/2008 | |
| WO | WO-2009/098246 A1 | 8/2009 | |

OTHER PUBLICATIONS

Kresowik et al. "Bacillus Calmette—Guerin immunotherapy for urothelial carcinoma of the bladder" Immunotherapy. Mar. 1, 2009; 1(2): 281-288.*
Bermudes, D., et al. (2002), "Live bacteria as anticancer agents and tumor-selective protein delivery vectors", *Current Opinion in Drug Discovery & Development*, 5(2): 194-199.
International Search Report dated Jul. 7, 2014 issued in PCT Patent Application No. PCT/EP2014/059392.
Vendrell, A., et al. (2011), "A novel *Salmonella typhi*-based immunotherapy promotes tumor killing via an antitumor Th1-type cellular immune response and neutrophil activation in a mouse model of breast cancer", *Vaccine*, 29: 728-736.

* cited by examiner

*Primary Examiner* — Louise W Humphrey
*Assistant Examiner* — Stephen A Perkins
(74) *Attorney, Agent, or Firm* — Harness, Dickey & Pierce, P.L.C.

(57) ABSTRACT

The present invention relates to a pharmaceutical composition comprising a live attenuated non-recombinant mutant of *Salmonella enterica* serovar *typhi* strain and/or a non-viable attenuated non-recombinant mutant of *Salmonella enterica* serovar *typhi* strain for use the treatment of cancer recurrence/progression. Preferably the cancer is bladder cancer.

8 Claims, 7 Drawing Sheets

A

B

SALMONELLA STRAINS FOR USE IN THE TREATMENT AND/OR PREVENTION OF CANCER

PRIORITY STATEMENT

Figure 1A:
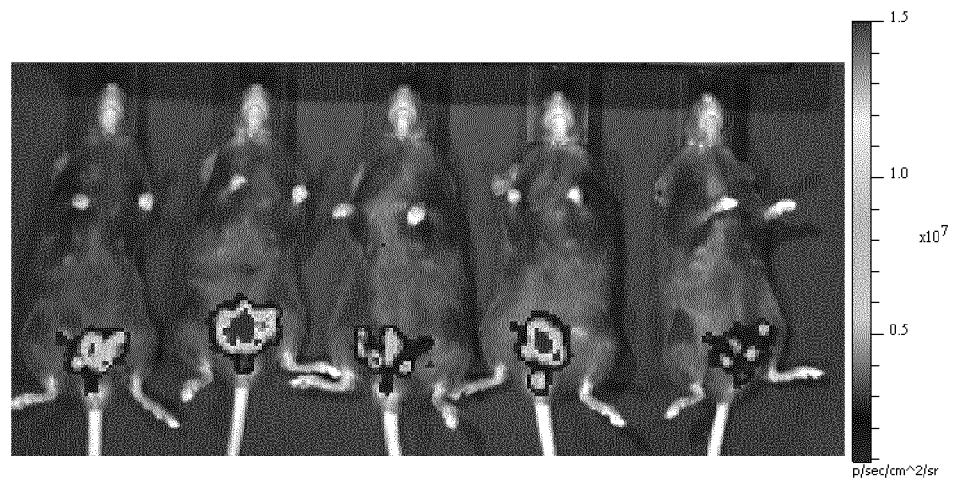

This application is a national stage application under 35 U.S.C. §371 of PCT International Application No. PCT/EP2014/059392 which has an International filing date of 7 May 2014, and claims priority under 35 U.S.C. §119 to European Application No. 13166851.9 filed 7 May 2013. The contents of each application recited above are incorporated herein by reference in their entirety.

FIELD OF INVENTION

The present invention relates to a pharmaceutical composition comprising a live attenuated non-recombinant mutant of *Salmonella enterica* serovar *typhi* strain and/or a non-viable attenuated non-recombinant mutant of *Salmonella enterica* serovar *typhi* strain for use in the treatment of cancer. Preferably the cancer is bladder cancer.

BACKGROUND OF THE INVENTION

Bladder cancer is the 4th most common cause of cancer in men both in Europe and USA Three-quarters of tumors are diagnosed as non muscle-invasive (NMIBC) and remain confined to the bladder mucosa. According to specific tumor stage and grade characteristics, intravesical (ives) immunotherapy with *Bacillus* Calmette-Guerin (BCG) partially limit the high propensity of these tumors to recur and possibly progress after transurethral endoscopic resection. BCG reduces recurrence and progression of bladder cancer. However, side effects linked to either the ability of BCG bacteria to infect bladder tissues and possibly disseminate or the strong inflammation induced are encountered in close to 90% of the patients, ranging from cystitis to sepsis and death.

The precise mechanism of action of BCG remains unknown. However it was shown that after ives instillation BCG infects and is internalized by the urothelial and cancer cells and elicits a huge influx of inflammatory cells and cytokines that leads to an anti-tumor response (reviewed in (Askeland, Newton, O'Donnell, & Luo, 2012). Some strategies like combining cytokines with BCG, reducing doses of BCG, using mycobacterial cell wall to replace BCG, or using toll-like receptor (TLR) agonist to stimulate the immune system were tested in clinical trials or animal models (reviewed in (Kresowik & Griffith, 2009)), however BCG has remained the best option to date for reducing recurrence/progression of NMIBC. Two studies using ives TLR agonists have shown therapeutic potential in the MB49 orthotopic bladder cancer model, the first showing that CpG, a TLR 9 agonist, was superior to BCG therapy (Mangsbo, Nanalga, Essand, Loskog, & Totterman, 2008) and the second showing that R-837 had an antitumor effect in this model (Hayashi et al., 2010). Similarly, Seow et al., have also recently reported anti-tumor effect of ives *lactobacillus* (Seow et al., 2010).

Numerous attempts to develop compositions comprising attenuated recombinant bacteria and/or attenuated tumor-targeted bacteria, especially attenuated *Salmonella typhi*, for the inhibition of the growth or reduction of the volume of a solid tumor cancer have been attempted such as, e.g. WO03/063593 (Vion Pharmaceuticals); US2007/0298012 (I. King & L.-M. Zheng); WO2009/098246 (Aeterna Zentaris GmbH); WO2006/076678 (Univ. John Hopkins) and but none of them have achieved sustainable efficacy in human clinical trials (Chorobik, Czaplicki, Ossysek, & Bereta, 2013).

For these reasons, there is still a need to provide a composition that is safer and more efficient than BCG to treat cancer, in particular bladder cancer.

SUMMARY OF THE INVENTION

The present invention concerns a pharmaceutical composition comprising a live attenuated non-recombinant mutant of *Salmonella enterica* serovar *typhi* strain and/or a non-viable attenuated non-recombinant mutant of *Salmonella enterica* serovar *typhi* strain for use in the treatment of bladder cancer.

The present invention also provides a method for inducing apoptosis in a cancer cell, said method comprising administering a pharmaceutical composition comprising a live attenuated non-recombinant mutant of *Salmonella enterica* serovar *typhi* strain and/or a non-viable attenuated non-recombinant mutant of *Salmonella enterica* serovar *typhi* strain.

Another objection concerns a method of treatment of bladder cancer comprising administering a pharmaceutical composition comprising a live attenuated non-recombinant mutant of *Salmonella enterica* serovar *typhi* strain and/or a non-viable attenuated non-recombinant mutant of *Salmonella enterica* serovar *typhi* strain wherein said viable or non-viable attenuated non-recombinant mutants of *Salmonella enterica* serovar *typhi* strain do not persist in the tumor and are selected from the group comprising Ty21a, CVD 908-htrA, CVD 909, Ty800, M01ZH09, $\chi$9633, $\chi$9639, $\chi$9640, and $\chi$8444.

A further object of the present invention is to provide a method for inducing apoptosis in a cancer cell, said method comprising administering a pharmaceutical composition comprising a live attenuated non-recombinant mutant of *Salmonella enterica* serovar *typhi* strain and/or a non-viable attenuated non-recombinant mutant of *Salmonella enterica* serovar *typhi* strain.

Also provided is the use of a live attenuated non-recombinant mutant of *Salmonella enterica* serovar *typhi* strain and/or a non-viable attenuated non-recombinant mutant of *Salmonella enterica* serovar *typhi* strain in the preparation of a medicament for the treatment of bladder cancer characterized in that said viable or non-viable attenuated non-recombinant mutants of *Salmonella enterica* serovar *typhi* strain do not persist in the tumor and are selected from the group comprising Ty21a, CVD 908-htrA, CVD 909, Ty800, M01ZH09, $\chi$9633, $\chi$9639, $\chi$9640, and $\chi$8444.

FIGURES

Figure 1B:
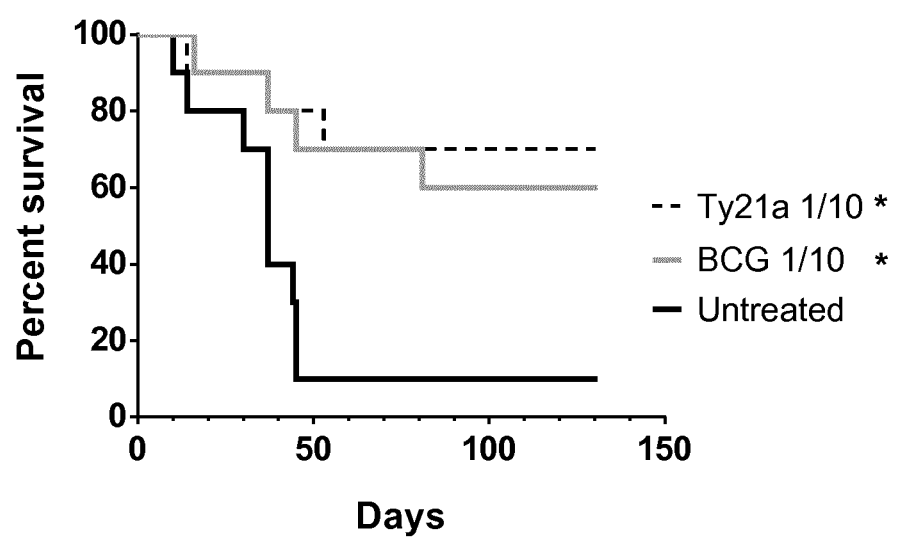

FIG. 1. Comparison of orthotopic bladder tumor regression upon BCG or Ty21a treatments. Groups of 10-20 female C57BL/6 mice were ives instilled with 200,000 MB49-luc cells after EtOH 22% pre-treatment (day 0). Tumor growth was monitored using an in vivo imaging system Xenogen, that can detect bioluminescence, a representative result is shown in (A) of tumor-bearing mice at day 8. At day 1, 8, 15 and 22, groups of mice were ives treated with different doses of BCG or Ty21a, while one group of mice remained untreated. The treatments varied from $\frac{1}{10}$ of the initial capsule of Ty21a or vial of BCG (B), to $\frac{1}{100}$ and $\frac{1}{1000}$ (C). Percentages of mice survival upon time are shown for each group. Significant differences following adjusted log-rank test are indicated as *p<0.025 in B or *<0.0125, p<0.0025 and *p<0.00025 in C.

Figure 2:
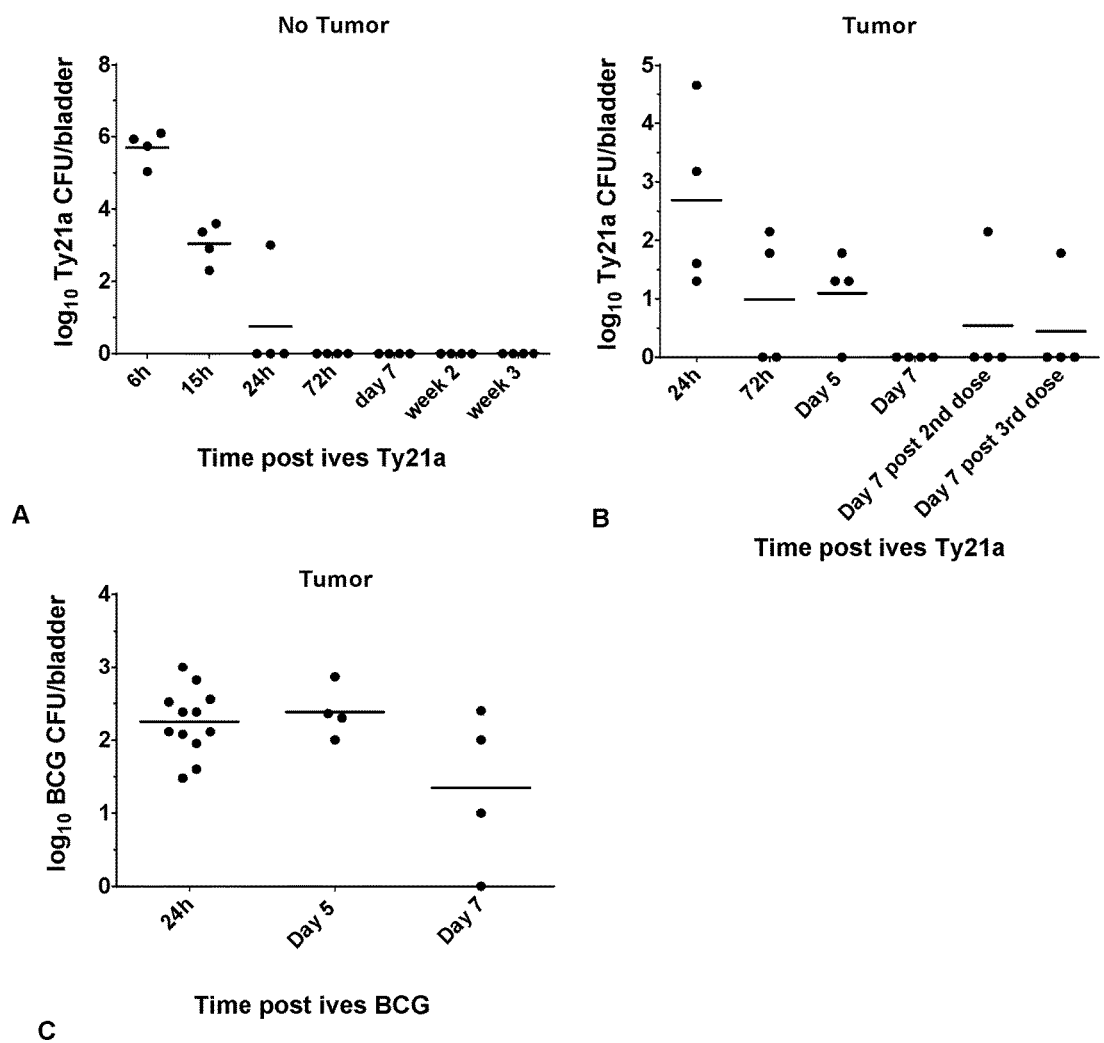

FIG. 2. Recovery of bacteria from the bladder after Ty21a or BCG treatments. Seven groups of four mice were ives challenged with Ty21a at day 0 (mean±SEM $1.3 \times 10^8 \pm 4.3 \times 10^7$ CFU/mice) (A). Six groups of mice were ives challenged with 200,000 MB49-luc cells at day −1 and 24 h later treated with Ty21a at day 0 (mean±SEM $3.9 \times 10^8 \pm 2.4 \times 10^8$ CFU/mice) (B) or BCG ($2$-$8 \times 10^7$ CFU/mice) (C). Mice were sacrificed at different time points after infection. Bladders were processed and plated as described in materials and methods. Data are expressed as number of CFU per tissue. The horizontal bar represent the mean responses.

Figure 3:
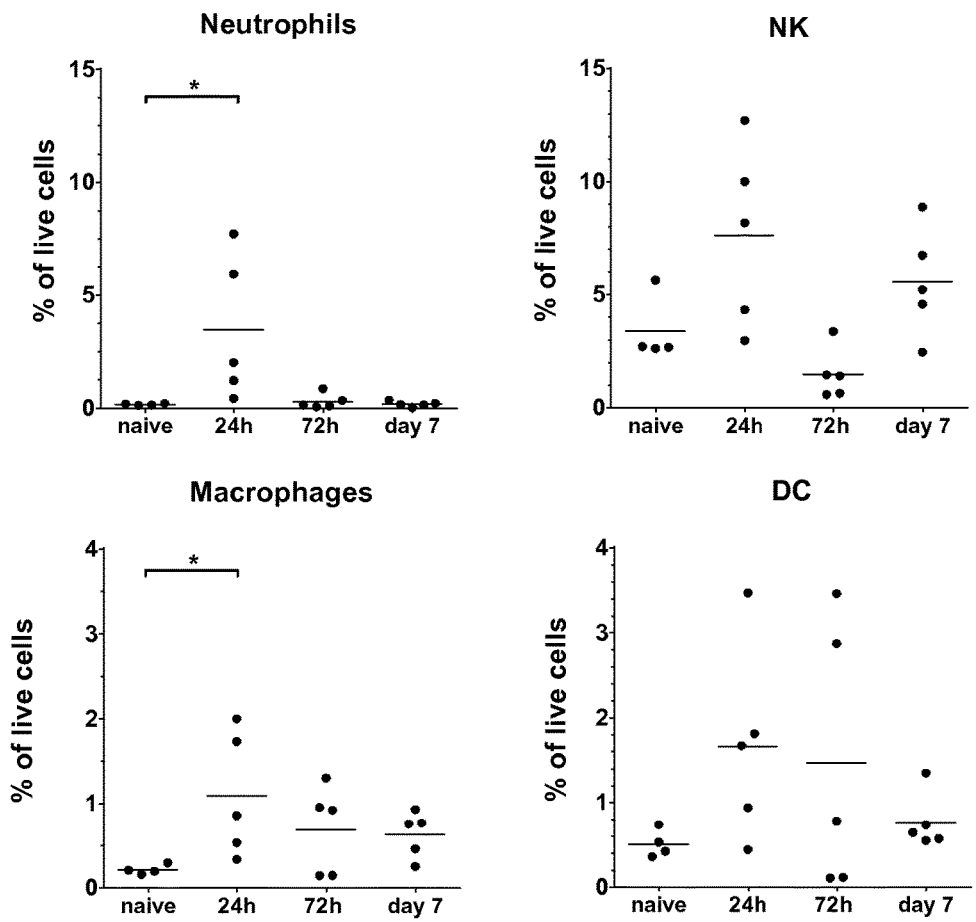
Figure 3:
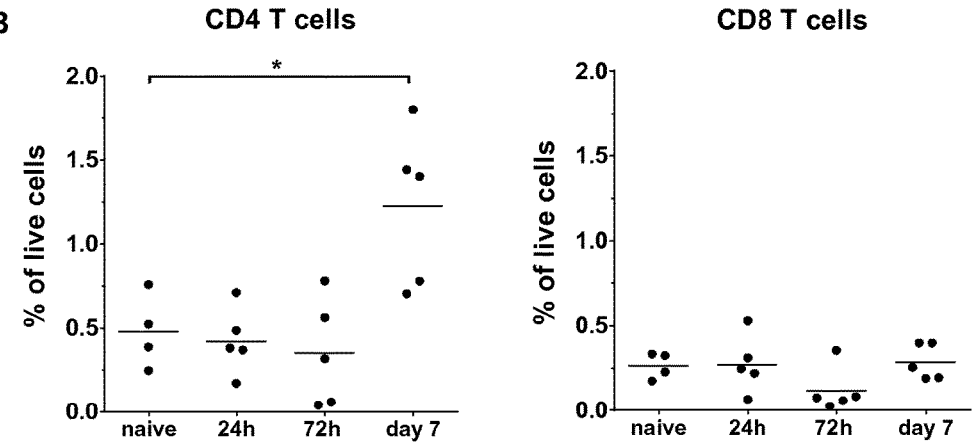

FIG. 3. Profile of innate and adaptive immune response in healthy bladder after a single dose of Ty21a. Groups of five mice were ives challenged with Ty21a (mean±SEM $1.3 \times 10^8 \pm 4.3 \times 10^7$ CFU/mice) at day 0, and sacrificed at different time points post-treatment. One group of four naïve mice was added. Bladder cells were recovered and flow cytometry stainings were performed. Dead cells were excluded with the aqua dead kit. The percentage of innate immune cells (A): Neutrophils, NK, macrophages and DC's, and adaptive immune cells (B): CD4 and CD8 T cells is shown. The horizontal bars represent the mean percentages. Significant differences between different time points and naïves are indicated following a One-way Anova, Dunnet's multiple comparison test *p<0.05.

Figure 4:
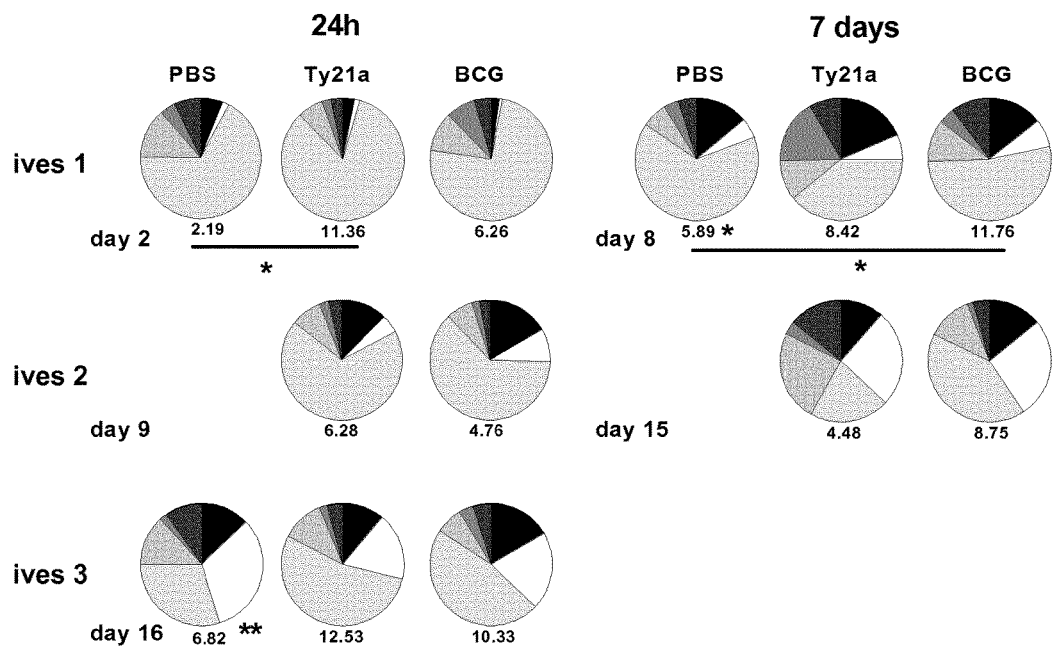

FIG. 4. Profile of innate and adaptive immune response in healthy bladder after a single dose of Ty21a. Groups of four to 10 mice were ives challenged with 200,000 MB49-luc cells at day 0 and treated with PBS, or 1/10 of BCG or Ty21a at days 1, 8, 15 and 22. Mice were sacrificed at different time points, 24 h after each treatment or seven days later. Bladder cancer cells were processed and recovered and flow cytometry stainings were performed. Dead cells were excluded with the aqua dead kit. The percentage of innate immune cells: NK, Neutrophils, macrophages and DC's, and adaptive immune cells: CD4 and CD8 T cells at each time point is represented as part of whole. The sum of the percentage of all cell populations is indicated below each pie chart. Significant differences are indicated following a One-way Anova, Dunnet's multiple comparison test *p<0.05.

Figure 5B:
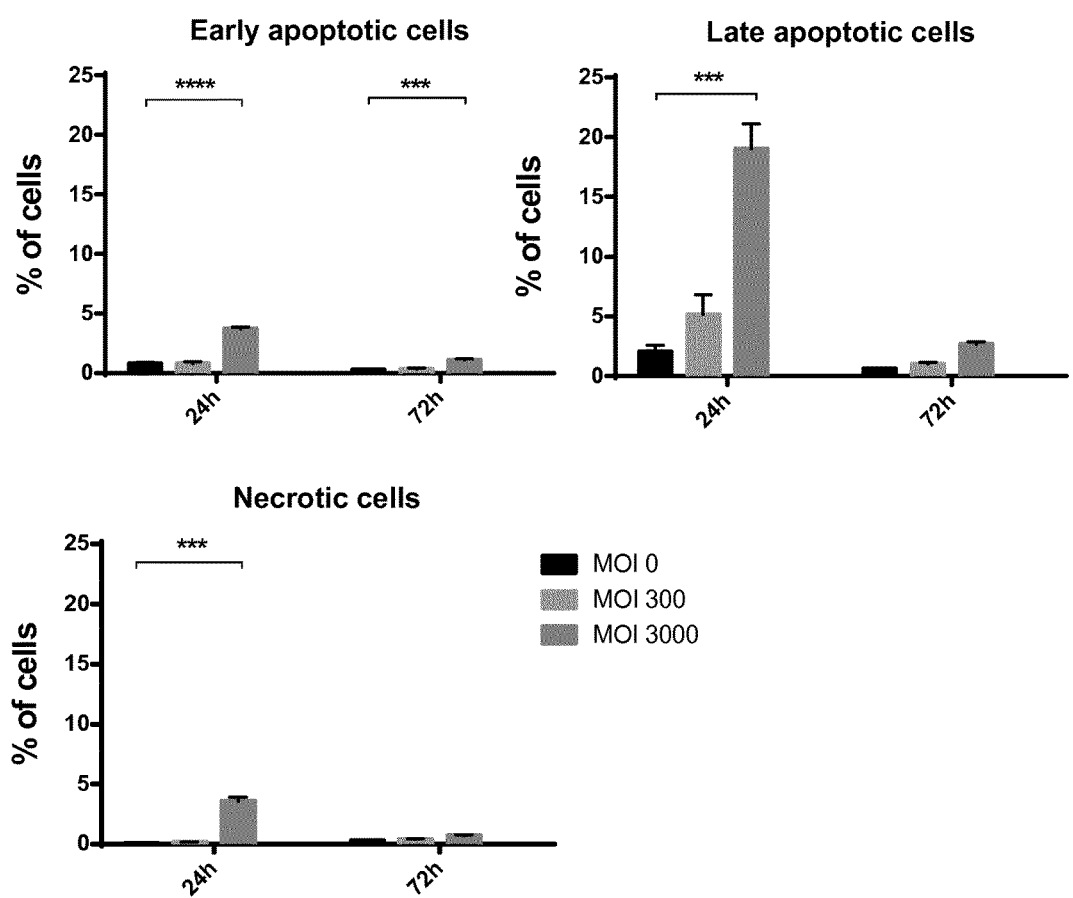
Figure 5A:
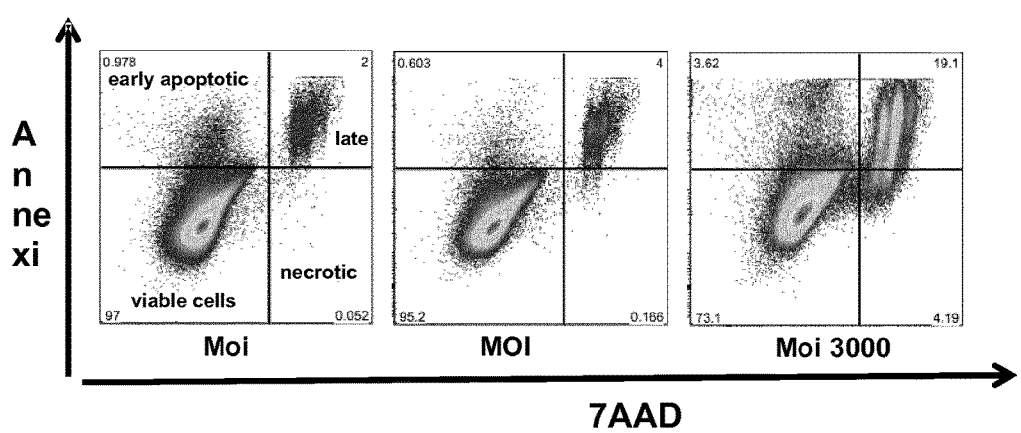

FIG. 5. MB49 percentage of apoptotic and necrotic cell populations. MB49 cell line was infected with different MOI of Ty21a and 24 h or 72 h later, cells were recovered and stained for Annexin V and 7AAD, and analyzed by flow cytometry. A representative plot is shown (A). Data are represented as the percentage of each cell population: early apoptotic cells, late apoptotic cells, and necrotic cells; three replicates per treatment, represented by mean and SEM (B). Significant differences between the treatment and control cells are shown by *p<0.001 or **p<0.0001 following a two-way ANOVA.

Figure 6:
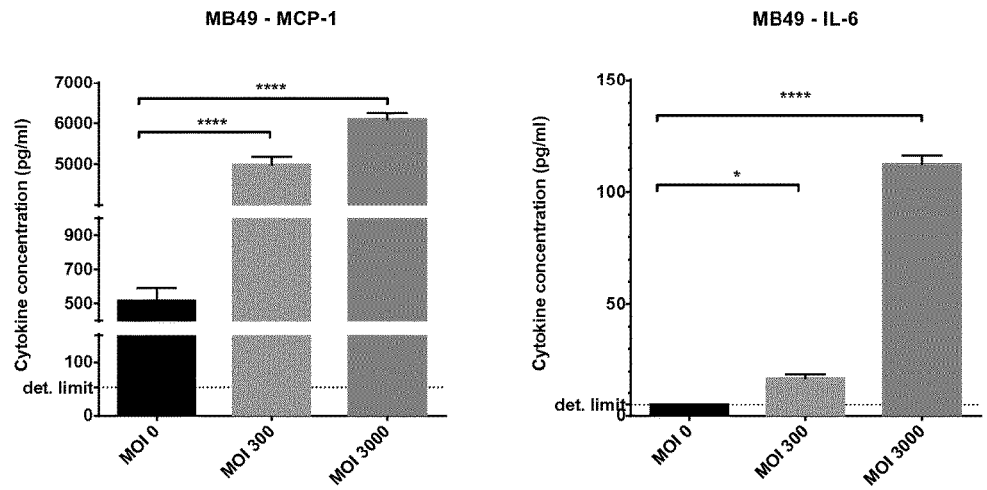

FIG. 6. Concentration of inflammatory cytokines secreted by MB49 cells. MB49 cell line was infected with different MOI of Ty21a and 24 h later cell supernatants were analyzed for inflammatory cytokines secretion using a Murine Inflammation Kit to detect and quantify IL-12p70, TNF, IFN-γ, MCP-1, IL-10 and IL-6 cytokines Two cytokine were detected MCP-1 and IL-6. Each bar corresponds to the cytokine concentration of the corresponding treatment; three replicates per treatment, represented by mean and SEM. Significant differences between each treatment and control (MOI 0) are shown by *p<0.05, *p<0.001 and **p<0.0001 following a One-way Anova, Dunnet's multiple comparison test.

Figure 7A:
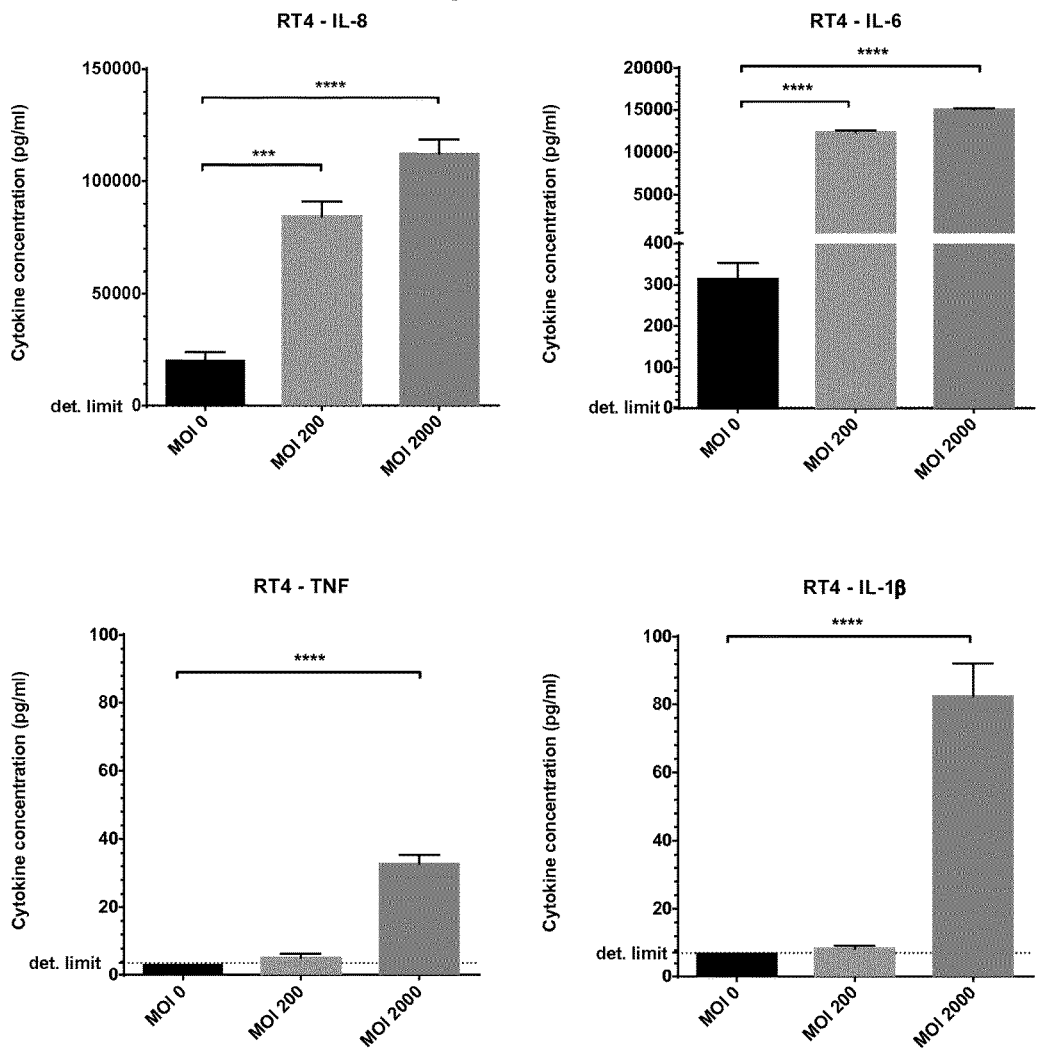
Figure 7B:
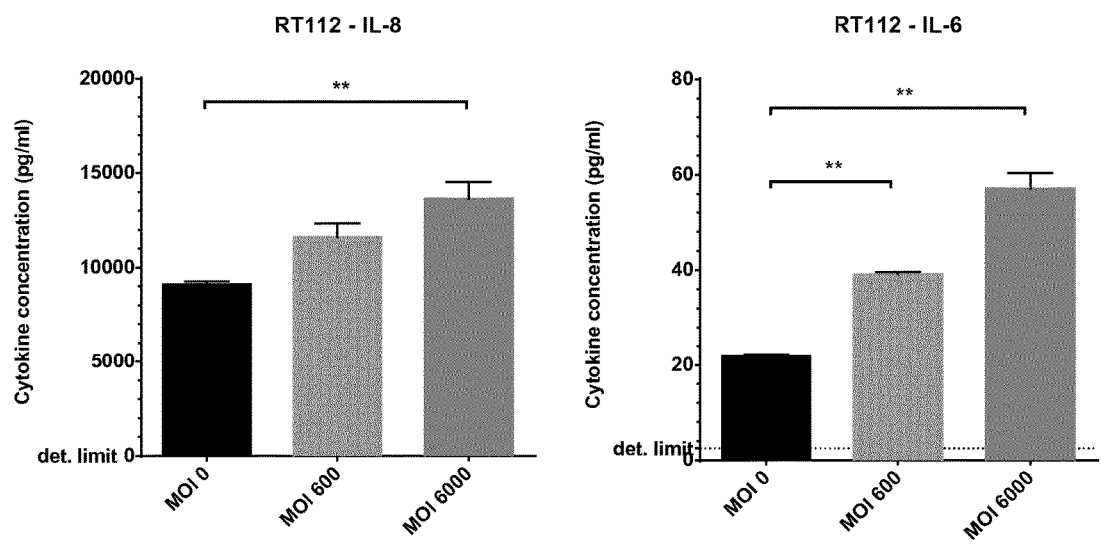

FIG. 7. Concentration of inflammatory cytokines secreted by human urothelial cell lines. Both human urothelial cell lines RT4 (A) and RT112 (B) were infected with different MOI of Ty21a and 24 h later cell supernatants were analyzed for inflammatory cytokines secretion using a inflammation Kit to detect and quantify IL-12p70, TNF, IFN-γ, MCP-1, IL-10 and IL-6 cytokines, or a Human Inflammation kit to detect and quantify IL-12p70, TNF, IL-10, IL-6, IL-1β and IL-8. Each bar corresponds to the cytokine concentration of the corresponding treatment; three replicates per treatment, represented by mean and SEM. Significant differences between each treatment and control (MOI 0) are shown by *p<0.05, *p<0.001 and **p<0.0001 following a One-way Anova, Dunnet's multiple comparison test.

DETAILED DESCRIPTION OF THE INVENTION

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

Unless defined otherwise, all technical and scientific terms used herein have the same meaning as is commonly understood by one of skill in art to which the subject matter herein belongs. As used herein, the following definitions are supplied in order to facilitate the understanding of the present invention.

The term "comprise" or "comprising" is generally used in the sense of include/including, that is to say permitting the presence of one or more features or components. Additionally, the term "comprising" also encompasses the term "consisting".

As used in the specification and claims, the singular form "a", "an" and "the" include plural references unless the context clearly dictates otherwise.

As used herein, "at least one" means "one or more."

Surprisingly, the Applicants of the present invention have shown that a pharmaceutical composition comprising live (or viable) attenuated non-recombinant mutant of *Salmonella enterica* serovar *typhi* strain and/or a non-viable attenuated non-recombinant mutant of *Salmonella enterica* serovar *typhi* strain is useful in the treatment of cancer.

The cancer may be selected from the non-limiting cancer group comprising melanoma, colon cancer, bladder cancer, breast cancer, prostate cancer, lung cancer carcinoma, lymphoma, blastoma, sarcoma, liposarcoma, neuroendocrine tumor, mesothelioma, schwanoma, meningioma, adenocarcinoma, leukemia, lymphoid malignancy, squamous cell cancer, epithelial squamous cell cancer, small-cell lung cancer, non-small cell lung cancer, adenocarcinoma of the lung, squamous carcinoma of the lung, cancer of the peritoneum, hepatocellular cancer, gastric or stomach cancer, gastrointestinal cancer, pancreatic cancer, glioblastoma, cervical cancer, ovarian cancer, liver cancer, hepatoma, rectal cancer, colorectal cancer, endometrial or uterine carcinoma, salivary gland carcinoma, kidney or renal cancer, vulval cancer, thyroid cancer, hepatic carcinoma, anal carcinoma, penile carcinoma, testicular cancer, esophageal cancer, a tumor of the biliary tract, and head and neck cancer.

Preferably the cancer is bladder cancer, most preferably a non-muscle invasive bladder cancer.

In case of bladder cancer, the pharmaceutical composition of the invention is preferably administered locally in the bladder, most preferably by instillation such as by intravesical instillation (ives).

The pharmaceutical composition can be administered locally in the bladder several times. After the initial administration (first administration), the pharmaceutical composition of the invention may be readministered every 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, or 24 weeks, but preferably every 1-2 week. For example, the patient may be treated every 1 week, receiving a maximum of 6 instillations, depending on the pharmaceutical composition and the cancer to be treated.

Other routes of administration can be suitable depending on the cancer to be treated. The form of administration of the pharmaceutical composition may then be systemic or topical. For example, the pharmaceutical composition of the invention may be administered by any convenient route, including oral, buccal, sublingual, parenteral, transdermal, vaginal, rectal, etc.

Generally, the treatment with a pharmaceutical composition of the invention consists in reducing or limiting the recurrence and/or progression of cancer (for example bladder cancer).

As used herein, "attenuated *Salmonella* strain" refers to a *Salmonella* mutant, i.e. different from the wild type, which is substantially not infecting/persisting in tissues and substantially incapable of reverting to full virulence when administered at a pharmaceutically effective dose. Preferably, the live attenuated mutant of *Salmonella enterica* serovar *typhi* strain and/or non-viable attenuated mutant of *Salmonella enterica* serovar *typhi* strain of the invention are non-recombinant. This term "non-recombinant" refers to the fact that these strains do not contain genes from other genera or species and/or do not express recombinant proteins. This is in contrast to what is known from the prior art and in particular from the following patent documents: US2007/0298012 (I. King & L.-M. Zheng); WO2009/098246 (Aeterna Zentaris GmbH); WO2006/076678 (Univ. John Hopkins); U.S. Pat. No. 6,962,696 (D. Bermudes et al.); WO98/15631 (Fond. pour le perfectionnement et la recherche en gynécologie-obstétrique); WO2008/091375 (Gov. Of the US) and WO2005/123762 (Indian Immunologicals Ltd). The strains described in the above-mentioned patent/patent applications are all recombinant strains in that they contain genes from other genera or species and/or express recombinant proteins and the *Salmonella* strains are used as carrier targeting the tumor. Usually, the genes from other genera or species that are contained in the strains described in the above prior art encode for recombinant proteins directed to tumor or cancer cells.

"A pharmaceutically effective dose" refers to a chemical material or compound which, when administered to a human or animal organism induces a detectable pharmacologic and/or physiological effect. In the present invention, a pharmaceutically effective dose of a live attenuated non-recombinant mutant of *Salmonella enterica* serovar *typhi* strain and/or a non-viable non-recombinant attenuated mutant of *Salmonella enterica* serovar *typhi* strain induces efficient tumor or cancer regression and/or limitation of the recurrence/progression of the tumor or cancer.

Typically, the pharmaceutical composition of the invention may significantly reduce the size or volume of the tumor by, 2% or more, 3% or more, 4% or more 5% or more, such as by 10% or more, such as by 20% or more, such as by 30% or more, such as by 50% or more, such as by 90%) or more, such as 95% or more, or significantly reduce the histological stage of a recurrent tumor (for instance from a low to a high stage), as compared to a suitable control.

The pharmaceutically effective dose of the live attenuated non-recombinant mutant of *Salmonella enterica* serovar *typhi* strain and/or non-viable attenuated non-recombinant mutant of *Salmonella enterica* serovar *typhi* strain may be determined by the artisan skilled in the art and may be based on the patient's clinical condition, as well as potency of the pharmaceutical composition, use and type of adjuvant or formulation, route and schedule of administration, immune status of the recipient, body weight, etc. Preferably, the pharmaceutical composition comprises a live attenuated non-recombinant mutant of *Salmonella enterica* serovar *typhi* strain and/or a non-viable attenuated non-recombinant mutant of *Salmonella enterica* serovar *typhi* strain of at least about $1\times10^8$ colony-forming units and $1\times10^8$ bacterial cells, most preferably $1\times10^9$ colony-forming units and $1\times10^9$ bacterial cells, even more preferably $2\times10^9$ colony-forming units and $5\times10^9$ bacterial cells, in a pharmaceutically acceptable carrier or diluent, such as, but not limited to, phosphate buffered saline (PBS).

Attenuated *Salmonella* strains have been used for years now in murine models for cancer treatments, due to their unique capability to specifically target tumor cells: these bacteria are facultative anaerobic that can grow in hypoxic or necrotic tumor areas resulting in tumor regression in mice (reviewed in (Wall, Srikanth, & McCormick, 2010)). However, this was not translated in cancer patients, where intravenous injection of an attenuated *Salmonella enterica* serovar *Typhimirium* did not demonstrate a preferential tumor colonization and/or induction of subsequent tumor regression (Toso et al., 2002). In contrast to this publication and to the existing prior art, the live attenuated non-recombinant mutant of *Salmonella enterica* serovar *typhi* strain and/or non-viable attenuated non-recombinant mutant of *Salmonella enterica* serovar *typhi* strain of the invention do(es) not grow in the cancer tissue, for example bladder cancer tissue, as shown in example 2. As a consequence, the live attenuated non-recombinant mutant of *Salmonella enterica* serovar *typhi* strain and/or non-viable attenuated non-recombinant mutant of *Salmonella enterica* serovar *typhi* strain of the invention do(es) not persist in the tumor or cancer tissue in contrast to what is known from the prior art.

Usually, the *Salmonella enterica* serovar *Typhi* strain of the invention is selected from the group comprising Ty21a, CVD 908-htrA, CVD 909, Ty800, M01ZH09 or χ9633, χ9639 and χ9640, χ8444.

These strains are referenced in the following literature: Levine M M, Tacket C O, Sztein M B. Host-*Salmonella* interaction: human trials. Microbes Infect 2001; 3:1271-9; Levine M M. Typhoid fever vaccines. In: Plotkin S A, Mortimer E A, eds. Vaccines, 2nd ed. Philadelphia: W. B. Saunders, 1994:597-633; Crump J A, Luby S P, Mintz E D. The global burden of typhoid fever. Bull World Health Organ 2004; 82:346-53; Levine M M, Galen J E, Tacket C O, Barry E M, Pasetti M F, Sztein M B. Attenuated strains of *Salmonella enterica* serovar *Typhi* as live oral vaccines against typhoid fever. In: Levine M M, Kaper J B, Rappuoli R, Liu M, Good M, eds.

New generation vaccines, 3rd ed. New York: Marcel Dekker, 2004:479-86; Shi H, Santander J, Brenneman K E, Wanda S Y, Wang S, Senechal P, Sun W, Roland K L, Curtiss R. Live recombinant *Salmonella Typhi* vaccines constructed to investigate the role of rpoS in eliciting immunity to a heterologous antigen. PLoS One. 2010 Jun. 18; 5(6)). The teachings of these articles are incorporated herein in their entirety.

Preferably, the non-recombinant *Salmonella enterica* serovar *Typhi* strain is Ty21a. Ty21a is usually found in the form of an oral vaccine that is known to be safe (Begier, Burwen, Haber, Ball, & Vaccine Adverse Event Reporting System Working, 2004; Engels, Falagas, Lau, & Bennish, 1998), and quite sensible to antibiotics if a general infection should occur. It has previously been shown that oral immunization of human Ty21a induces specific CD8 T cells, which secrete inflammatory cytokines such as IFN-γ, TNF-α and IL-2. In mice, other attenuated *Salmonella Typhi* strains have been shown to induce a Th1-type immune response.

In contrast to this publication and to the existing prior art, the live attenuated non-recombinant mutant of *Salmonella enterica* serovar *typhi* strain and/or non-viable attenuated non-recombinant mutant of *Salmonella enterica* serovar *typhi* strain of the invention are i) not transformed with genes from other genera or species, ii) do not express one or more heterologous protein(s) or antigen(s) and/or iii) do not act as vaccine carriers.

Referring to the examples, the Applicants have performed a side by side comparison of the ability of ives Ty21a and BCG treatments to regress established murine orthotopic MB49-luc tumors suggested a better efficacy of Ty21a, as efficient tumor regression was maintained with 100-fold lower doses.

Previous studies have been conducted trying to replace BCG therapy for bladder cancer. Using a TLR-9 agonist, CpG, different studies have shown the ability to regress both s.c. (Hegele et al., 2004; Loskog et al., 2005) or bladder (Hegele et al., 2005; Mangsbo et al., 2008; Ninalga, Loskog, Klevenfeldt, Essand, & Totterman, 2005) MB-49 tumors. However, only Mangsbo et al. (Mangsbo et al., 2008), demonstrated that this therapy was superior to BCG. The studies that examined the effect of other bacterial strains used probiotic. Both ives instillation of heat-killed *Lactobacillus casei* (Takahashi et al., 2001), or live *Lactobacillus rhamnosus* GG (Seow et al., 2010) resulted in bladder tumor regression similar to BCG. Our data show that in healthy bladders treated with Ty21a, it could be observed a transient infiltration of neutrophils and macrophages. Moreover, the frequency of CD4 T-cells was increased one week after instillation. During ives BCG treatment of patients, the main population of immune cells present in the bladder was neutrophils corresponding to 75% of cells present in urines, followed by macrophages and NK cells (De Boer et al., 1991). In mice, at early time points, BCG induced an acute bladder inflammation with an important infiltration of neutrophils, and by day 21 to 28 there is a substantial increase of macrophages (Saban et al., 2007). Moreover, in these mice there was a bladder edema formation, and the inflammation levels were maintained for up to three weeks following discontinuation of the therapy, contrasting with our observations with Ty21a. As bacteria did not persist in bladders and inflammatory cell infiltration was transient Applicants have shown that Ty21a induces less adverse events than BCG, which persist in bladder and induces an important inflammatory response, responsible for a large part of adverse events suffered by patients (Alexandroff, Jackson, O'Donnell, & James, 1999). Moreover, Ty21a was unable to infect both murine and human urothelial cell lines, suggesting that in humans it may be unable to infect urothelial cells, reducing risks of dissemination, and improving safety.

The particular pharmaceutically acceptable carrier and/or diluent employed in the pharmaceutical compositions of the invention are conventional in the art. Examples of diluents include: buffers for buffering against gastric acid in the stomach, such as citrate buffer (pH 7.0) containing sucrose, bicarbonate buffer (pH 7.0) alone (Black et al., 1990; Levine, Ferreccio, Black, Tacket, & Germanier, 1989), or bicarbonate buffer (pH 7.0) containing ascorbic acid, lactose, and optionally aspartame (Levine et al., 1988). Examples of carriers include: proteins, e.g., as found in skim milk; sugars, e.g., sucrose; or polyvinylpyrrolidone.

For example, the pharmaceutical composition Vivotif® (Typhoid Vaccine Live Oral Ty21a) comprises the Ty21a strain that is grown in fermentors under controlled conditions in medium containing a digest of yeast extract, an acid digest of casein, dextrose and galactose. The bacteria are then collected by centrifugation, mixed with a stabilizer containing sucrose, ascorbic acid and amino acids, and lyophilized. The lyophilized bacteria are mixed with lactose and magnesium stearate and filled into gelatin capsules which are coated with an organic solution to render them resistant to dissolution in stomach acid.

Contents of one enteric-coated capsule of Vivotif® (Typhoid Vaccine Live Oral Ty21a) * are shown in Table 1

TABLE 1

| | |
|---|---|
| Viable *S. typhi* Ty21a | 2-6.8 × 10$^9$ colony-forming units* |
| Non-viable *S. typhi* Ty21a | 5-50 × 10$^9$ bacterial cells |
| Sucrose | 26-130 mg |
| Ascorbic acid | 1-5 mg |
| Amino acid mixture | 1.4-7 mg |
| Lactose | 100-180 mg |
| Magnesium stearate | 3.6-4.4 mg |

*Source: manufacturer (Crucell) indication for the FDA (version 2006)

In case the *Salmonella enterica* serovar *Typhi* strain Ty21a is to be administered by ives instillation, then the capsule of the oral vaccine Vivotif for Ty21a is, for example, reconstituted in buffer, preferably PBS, most preferably sterile PBS.

Alternatively, or additionally, the compositions of the invention described herein may be administered alone or in combination with other treatments, therapeutics or agents, either simultaneously or sequentially dependent upon the cancer to be treated. For example, the compositions of the invention may be administered in association with radiotherapy, chemotherapy or immunotherapy, or a combination thereof.

The present invention also relates to a method for inducing apoptosis in a cancer cell, said method comprising administering a pharmaceutical composition comprising a live attenuated non-recombinant mutant of *Salmonella enterica* serovar *typhi* strain and/or a non-viable attenuated non-recombinant mutant of *Salmonella enterica* serovar *typhi* strain.

Typically, the pharmaceutical composition of the invention may increase specifically the apoptosis in cancer cells at a given concentration. For example, methods of the invention may increase the rate of apoptosis in cancer cells by 2% or more, such as by 5% or more, such as by 10% or more, such as by 25% or more, such as by 50% or more, such as by 75% or more, such as by 100% as compared to a suitable control.

The invention also relates to the use of a live attenuated non-recombinant mutant of *Salmonella enterica* serovar *typhi* strain and/or a non-viable attenuated non-recombinant mutant of *Salmonella enterica* serovar *typhi* strain in the preparation of a medicament for the treatment of bladder cancer characterized in that said viable or non-viable attenuated non-recombinant mutants of *Salmonella enterica* serovar *typhi* strain do not persist in the tumor or cancer tissue. Preferably, the live attenuated non-recombinant mutant of *Salmonella enterica* serovar *typhi* strain and/or non-viable attenuated non-recombinant mutant of *Salmonella enterica* serovar *typhi* strain is selected from the group comprising Ty21a, CVD 908-htrA, CVD 909, Ty800, M01ZH09, χ9633, χ9639, χ9640, and χ8444.

Further encompassed in the present invention is a method of treatment and/or prevention of cancer, in particular bladder cancer, said method comprising administering a live attenuated non-recombinant mutant of *Salmonella enterica* serovar *typhi* strain and/or a non-viable attenuated non-recombinant mutant of *Salmonella enterica* serovar *typhi* strain to a patient in need thereof. Preferably, the live attenuated non-recombinant mutant of *Salmonella enterica* serovar *typhi* strain and/or non-viable attenuated non-recombinant mutant of *Salmonella enterica* serovar *typhi* strain is selected from the group comprising Ty21a, CVD 908-htrA, CVD 909, Ty800, M01ZH09, χ9633, χ9639, χ9640, and χ8444.

Also encompassed in the present invention is a method for promoting secretion of inflammatory cytokines by human cancer cell lines, which may participate in anti-tumor immune response and tumor regression in humans, said method comprising administering a pharmaceutical composition comprising a live attenuated non-recombinant mutant of *Salmonella enterica* serovar *typhi* strain and/or a non-viable attenuated non-recombinant mutant of *Salmonella enterica* serovar *typhi* strain.

Alternatively, or additionally, it will also become apparent that the pharmaceutical composition of the invention may be administered alone or in combination with other treatments, therapeutics or agents, either simultaneously or sequentially dependent upon the condition to be treated. For example, other treatments, therapeutics or agents may be suitable for treating cancer such as bladder cancer.

The foregoing description will be more fully understood with reference to the following examples.

EXAMPLES

Example 1: Material and Methods

Mice and Cell Culture

Eight- to ten-week-old female C57BL/6 WT mice (Charles River, L'Arbresle, France) were used following ethical directives of the Swiss veterinary authorities. MB49 cell line (kindly provided by Prof. A. Loskog, Uppsala University, Uppsala, Sweden) is a carcinogen-induced transitional cell carcinoma derived from a C57Bl/6 male mouse (Summerhayes & Franks, 1979). The human urothelial cell lines RT4 (Rigby & Franks, 1970) and RT112 (Masters et al., 1986) were kindly provided by Professor Thalmann, Bern, Switzerland. All cell lines were maintained in DMEM media (Dulbecco's modified Eagle's medium) supplemented with 10% fetal bovine serum (FBS), 100 U/ml penicillin and streptomycin and Hepes (10 mM) (all from Invitrogen, Life technologies, Zug, Switzerland). MB49 cells were infected with Lenti-luc to generate MB49-luc cells, as described in (Decrausaz et al., 2011). Luciferase expression was measured after addition of D-luciferin (final concentration of 0.15 mg/ml, Promega, Dübendorf, Switzerland) using a Fluostar Omega Luminometer (BMG Labtech, Offenburg, Germany).

BCG and Ty21a

BCG (oncoTICE®, Essex Chemie SA, Luzern, Switzerland), or Ty21a (Vivotif®, Crucell, Bern, Switzerland) were ives instilled by catheterization using Introcan 24G/3/4 (Braun, Melsungen, Germany) in anesthesized mice (as described hereafter) The heat-killed bacteria were obtained after water-bath-incubation for 30 minutes at 85° C. and then platted in order to confirm the killing. The dose of each bacteria instilled, as well as the determination of bacteria killing was confirmed by platting in LB agar (BD Difco, Basel, Switzerland) plates for Ty21a or M7H11 (Remel, Kans., USA) plates enriched with OADC (BD, Basel, Switzerland) for BCG. Ty21a capsules contained at least $2\times10^9$ viable bacteria and $5\text{-}50\times10^9$ dead bacteria. Each BCG vial contains $2\text{-}8\times10^8$ bacteria. LB agar plates were incubated for 48 h at 37° C. while M7H11 plates were incubated for 4 weeks at 37° C., in a closed recipient and humidified once a week. Colonies growth in LB agar plates were tested with an agglutination test *Salmonella* O Antiserum group D1 factors 1, 9, 12 (BD Difco).

Challenge of Mice with Tumor Cells and Ives Treatment

The murine orthotopic model was performed as follow: mice were deeply anesthetized (i.p. anesthesia with a mixture of 10% Rompun (Bayer, Provet AG, Lyssach, Switzerland) and 10% Ketanarcon (Streuli Pharma, Uznach, Switzerland) in PBS (100 µl per 10 g of body weight)), and catheterized using Introcan 24G/3/4 (Braun, Melsungen, Germany), and 200,000 MB49-luc cells were instilled in bladder (day 1), after pretreatment with ethanol 22% for 15 minutes. Tumor growth was monitored by bioluminescence 15 minutes after ip injection of D-luciferin (Promega, 150 µg/g of body weight) in the Xenogen imaging system (Xenogen/Caliper Life Science, kindly provided by cellular imaging facility (CIF), UNIL, Lausanne, Switzerland). In tumor regression assay experiments, the treatments were performed on days 2, 9, 16 and 23 following the schedule published by (Mangsbo et al., 2008).

Bacterial Survival

In-vivo bacterial survival assay was performed by ives instillation in mice, that were sacrificed at different time points by CO2 inhalation, in order to recover spleen, BLN and bladders. Organs were homogenized in a sucrose solution, and then platted in LB or M7H11 depending of treatment received (Ty21a or BCG respectively).

For in-vitro bacterial survival assay, cell lines were infected with Ty21a at different MOI for 1.5 h at 37° C., then 50 µg/mL Gentamicin was added for 1 h at 37° C., in order to kill extracellular bacteria. Cell culture was maintained in 15 µg/mL Gentamicin (Gibco, Zug, Switzerland). At different time points, cells were lysed with 0.1% Triton-X-100 (Sigma-Aldrich, Buchs, Switzerland) and harvested for platting in LB agar plates.

Preparation of Murine Cell Suspensions

Mice were sacrificed by CO2 inhalation and BLN and bladder were harvested, and single-cell suspensions were obtained as previously described (Revaz, Debonneville, Bobst, & Nardelli-Haefliger, 2008). Briefly, BLN cell suspensions were obtained by mechanical dissociation. Bladders were minced and digested step-wise with 0.5 mg/ml thermolysin (Roche, Basel, Switzerland) and 1 mg/ml collagenase/dispase (Roche). All cell suspensions were resuspended in DMEM medium complemented with 10% FCS.

Flow Cytometry Labeling and Analysis

BLN and bladder cells were stained using the following monoclonal anti-mouse antibodies: PE-anti-CD11c (HL3, BD Biosciences, Basel, Switzerland), PE/TXRD-anti-CD8 (53-6.7, Southern Biotech, Birmingham, USA), eF450-anti-CD4 (GK15, eBiosciences, Vienna, Austria), FITC-anti-IA/IE (M5/114.15.2), PerCp/Cy5.5-anti-CD3 (17A2), PE/Cy7-anti-GR1 (RB6-8C5), APC-anti-CD11b (M1/70), AF700-anti-NK1.1 (PK136), APC/Cy7-anti-F4/80 (BM8) all from Biolegend (London, UK). Dead cells were stained with a live/dead fixable aqua dead cell stain kit (Invitrogen, Life technologies, Zug, Switzerland). Cells were acquired using a Gallios Flow cytometer (Beckman Coulter, Nyon, Switzerland) and analyzed with the FlowJo 9.6.1 software (Tree Star, Ashland, USA).

Cytokines Analysis

Supernatants of urothelial infected cells were recovered and stored at −80° C. until analysis. Human cell lines were analyzed using the BD Cytometric Bead Array (CBA) Human Inflammation Kit for detection and quantification of the following cytokines: IL-12p70, TNF, IL-10, IL-6, IL-1β and IL-8, following the manufacturer protocol. BD CBA Mouse Inflammation Kit was used to detect and quantify IL-12p70, TNF, IFN-γ, MCP-1, IL-10 and IL-6 cytokines for the MB49 cell line, following the manufacturer instructions. The samples were then analyzed with the BD FACSArray Bioanalyzer system.

Tumor Cell Apoptosis

MB49 cells were infected with different MOI of Ty21a alive or heat-killed. 24 h and 72 h post-infection, cells were recovered and stained with Annexin V and 7-AAD markers using the PE Annexin V apoptosis detection kit (BD), following manufacturer protocol. Cells were acquired using a Gallios Flow cytometer (Beckman Coulter) and analyzed with the FlowJo 9.6.1 software (Tree Star).

Statistical Analysis

Statistical analyses were performed using Prism 6.00 for Windows (GraphPad software, California, USA) as indicated in the text or in figure legends.

Example 2: Results

Ives Ty21a Treatment Increases Mice Survival in an Orthotopic Model of Bladder Cancer.

Figure 1C:
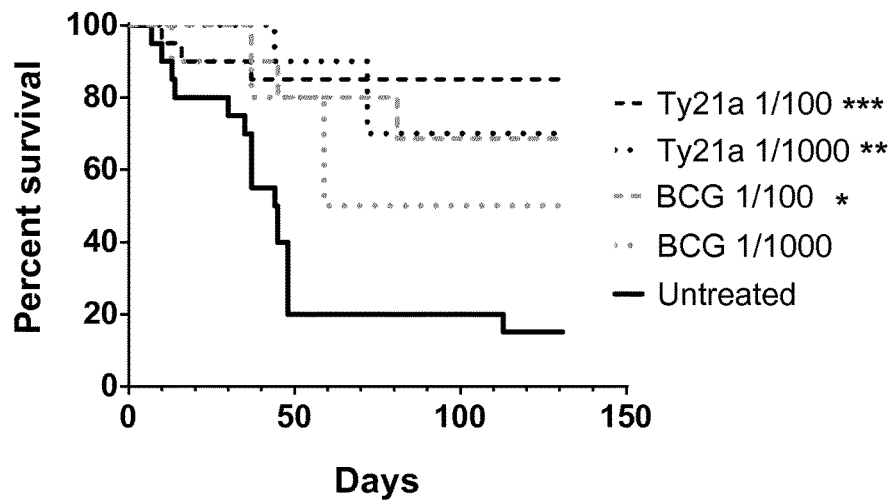

The potential of ives Ty21a to regress bladder tumors was assessed in the orthotopic bladder cancer model using MB49 cells. This mouse model resemble human superficial bladder cancer regarding cell surface markers, sensitivity to apoptosis and immunological profile (Chen, Zhang, Cao, Hessner, & See, 2009) and has been commonly used to understand and/or assess ives BCG immunotherapy (Loskog et al., 2005). To ensure bladder tumor monitoring, the inventors transduced MB49 cells with luciferase (luc)-expressing lentiviral vector to generate MB49-luc cells. In our setting a tumor-take close to 100% was obtained with 22% ethanol pretreatment before ives instillation of 200,000 MB49-luc cells (for representative experiment at day 8 see FIG. 1A). Three groups of 10 mice were ives instilled with 200,000 MB49-luc cells at day 0 and treated with BCG or Ty21a at day 1, 8, 15 and 22 or left untreated, following the usual schedule of BCG treatments in this model (Arnold, de Boer, O'Donnell, Bohle, & Brandau, 2004; Mangsbo et al., 2008). The doses of bacteria consisted in 1/10 of the reconstituted capsule of the oral vaccine Vivotif for Ty21a (at least $2 \times 10^9$ CFU/capsule) or vial of Oncotice for BCG ($2-8 \times 10^8$ CFU/vial). Percentages of mice surviving upon time are shown (FIG. 1B) for each group. Our data show that both Ty21a and BCG were able to regress tumors significantly compared to untreated mice. Ty21a led to regression of 7 out 10 mice (p=0.01 compared to untreated mice, using adjusted log-rank test), whereas BCG led to the regression of 6 mice out 10 (p=0.01). We observed that tumors continue to grow for about two weeks after the first treatment, but at time of the fourth instillation most mice had completely regressed tumors. We further assessed the effects of reduced bacterial doses (FIG. 1C). Five groups of mice that have been ives instilled at day 0 with 200,000 MB49-luc cells received 1/100 or 1/1000 of the inoculum of Ty21a or BCG ives at day 1, 8, 15 and 22 or left untreated. Both Ty21a doses (1/100 and 1/1000) induced tumor regression (17/20 mice and 7/10 mice regressed respectively), being both significantly different from controls (p=0.0002 and p=0.002, respectively). In contrast, only the BCG inoculum at 1/100 was significantly different from controls (p=0.0054), leading to the tumor regression of 7 out 10 mice. One-thousandth of the BCG vial induced tumor regression in 5 mice out 10, which was not significantly different from controls (p=0.024). Taken together, these results suggest that the Ty21a is more efficient in regressing orthotopic MB49 bladder tumors, than BCG as it was still effective at lower doses.

Ty21a Bacteria do not Persist in Healthy Bladder nor in Tumors

We first investigated whether Ty21a can infect and/or survive in mice bladder. We ives instilled Ty21a (mean±SEM 7.9±0.16 $\log_{10}$ CFU/mice) in different groups of 4 mice and sacrificed them at different time points (FIG. 2A). Our results showed that Ty21a is not able to persist in bladder for more than 24 h. Moreover, 6 hours post-instillation there was a considerable decrease of bacteria in bladder (100-fold less than those instilled), most probably due to micturation. We also determined the invasion to bladder draining lymph nodes (BLN) and spleen; however no bacteria were recovered from these organs, demonstrating the lack of Ty21a colonization and invasion. Since another *Salmonella enterica Typhi* strain showed a preferential niche in murine tumors after intratumoral injection (Vendrell et al., 2011), we examined whether ives Ty21a, may preferentially colonize tumors. We instilled different groups of 4 mice with 200,000 cells MB49-luc ives and 24 h later we ives instilled Ty21a (mean±SEM 8.19±0.27 $\log_{10}$ CFU/mice), two groups received a second dose one week later, and one of these received a third dose one week later. Mice were sacrificed at different time points, and CFU/organ determined (FIG. 2B). Our data shown that bacteria can be detected until day 5 in bladder-tumors, however 24 h after instillation the number of living bacteria was greatly decreased (up to 100,000-fold). One week after instillation we did not detect any bacteria in bladder tumors, and even after bacterial rechallenge persistence did not increase. Thus, Ty21a seemed to stay longer in bladder in presence of tumor, though in low amount, and again no bacteria were detected in BLN or spleen. This is in contrast to BCG (Biot et al., 2012) and our data in FIG. 2C) that can persist in bladder tumors for at least one week. In addition, BCG bacteria were also detected in bladder BLN five days after instillation in three out four mice. Altogether these results shows that Ty21a may be safer as it consistently persist only for less than 48 hours in bladder tumors as compared to at least 7 days for BCG and it did not invade deeper organs.

Ty21a Transiently Induces Local Inflammatory Cells in Bladder Mucosa

To assess safety of ives Ty21a we examined the inflammatory/immune cells that are attracted into the bladder. Mice receiving ⅒ of Ty21a capsule ives were sacrificed at different time points, and cells from bladder were stained and analyzed by flow cytometry (see Supplementary FIG. 1 for gating strategy). The infiltration of neutrophils, macrophages, Natural killer cells (NK) and dendritic cells (DC) was analyzed (FIG. 3A). We observed a robust infiltration of neutrophils 24 h after Ty21a instillation (mean±SEM % of 3.46±1.42 versus 0.16±0.02 in naïve mice, p<0.05 following a One-way Anova, Dunnet's multiple comparison test). This strong infiltration was transient with rapid return to control levels after 72 h. We also observed a significant increase of five-fold in macrophages 24 h after ives treatment (1.00±0.33 versus 0.21±0.03 in naïve mice, p<0.05), that slowly decreased at 72 h. Concerning NK and DC cells there was a slight but not significant increase 24 h after treatment. CD4 T cells were also significantly increased seven days after instillation (1.22±0.21 versus 0.48±0.11 in naïve mice, p<0.05) while CD8 T cell were not affected (FIG. 3B). This suggests that Ty21a induces only transiently a local inflammatory response in the bladder.

Repeated Ives Instillations of Live BCG or Ty21a Result in a Differential Infiltration of Lymphoid Cells into Bladder Tumors Leukocytes tumor infiltration was further examined upon repeated ives doses of BCG, Ty21a or PBS, as control. Mice ives instilled with MB49 tumor cells at day 0, received the ives bacteria or PBS at days 1, 8 and 15 and were sacrificed 24 h or seven days after each dose. Twenty-four hours after the first dose, Ty21a induced a robust infiltration of lymphoid cells (11.36% comparing to 2.19%, p<0.05, following a one-way ANOVA, Dunnett's multiple comparison test), whereas BCG induced a slight but not significant infiltration (6.26%). However, seven days later, BCG-induced infiltration was significantly increased (11.76% as compared with 5.89 in PBS treated mice, p<0.05), whereas Ty21a-infiltration was not different from PBS treated tumor-bearing mice. It is noteworthy that a significant tumor infiltration of lymphoid cells in the PBS-treated tumor-bearing mice appeared with time (p<0.05, at day 8 and p<0.01 at day 16, as compared to day 2), correlating with tumor growth. In this context, lymphoid cell tumor infiltration was not much affected by the 2nd bacterial treatment, except for a higher BCG-induced infiltration at day 15 (though not significant). A trend towards a bacterial-induced lymphoid cell infiltration was again observed 24 h after the 3rd dose. Our data suggest that Ty21a induce a high infiltration of inflammatory cells 24 h after each treatment, with a slow decrease with time. In contrast, BCG seems to induce higher infiltrations seven days after each dose. This suggest that Ty21a may be less inflammatory at long term, maybe reducing adverse events related to inflammation, when compared to BCG that induce a sustained inflammation.

Ty21a Induce Apoptosis of MB49 Cells

To clarify the mechanisms for Ty21a-mediated tumor regression, we investigate the ability of these bacteria to infect MB49 cells in vitro. This turned out not to be the case (data not shown), thus confirming the results obtained in the bladder (FIG. 2B). Next, we reasoned that Ty21a may possibly not infect murine cells, but only human cells, as it is a human-restricted pathogen.

However, infection of human bladder tumor cell lines RT4 and RT112 with Ty21a at a multiplicity of infection (MOI) up to 6000 did not show any invasion or survival. In contrast to Ty21a, it is well reported that BCG infects both murine and human tumor cell lines. We next examined whether Ty21a may have a direct effect on survival/apoptosis of tumor cells. MB49 cells were "infected" (this term will be used for addition of bacteria following the infection protocol) with different MOI, and 24 h or 72 h later, cells were recovered and stained for Anexin V and 7AAD, and analyzed by flow cytometry. Early apoptotic cells would only be positive to Anexin V, as the membrane integrity is assured, however late apoptotic cells would also be permeable to 7AAD. In addition necrotic cells would be discriminated as single positive for 7AAD (see FIG. 6A for representative schema). Our data show that Ty21a was able to induce apoptosis 24 h after "infection", with about 5% of cells that were in early apoptosis or necrosis and 20% being in late apoptosis after "infection" with high MOI of Ty21a (MOI 3000) (p<0.0001 when compared to MOI 0. These results suggest that Ty21a can trigger apoptosis and necrosis of tumor cells, within 24 h after bacterial contact.

Ty21a Induce Cytokine Secretion in Both Murine and Human Cell Lines

We next investigated the capability of Ty21a to induce secretion of inflammatory cytokines by urothelial cells, as it was previously shown for BCG (reviewed in (Alexandroff et al., 1999). Both murine (MB49) and human (RT4 and RT112) urothelial cell lines were "infected" with different MOI of Ty21a and 24 h later cell supernatants were analyzed for inflammatory cytokines secretion using a Murine Inflammation Kit (CBA) to detect and quantify IL-12p70, TNF, IFN-γ, MCP-1, IL-10 and IL-6 cytokines, or a Human Inflammation kit to detect and quantify IL-12p70, TNF, IL-10, IL-6, IL-1β and IL-8. Theoretical MOI were calculated according to the CFU range described for Ty21a capsules, and corrected afterwards by bacteria plating on LB plates, which explain differences in real MOI between experiments. Only two cytokines were detected in the MB49 cell supernatant, MCP-1 and IL-6 (FIG. 7). The MCP-1 cytokine was already secreted by untreated cells at high levels, however its secretion was significantly increased (more than 10-fold) after infection with Ty21a at MOI 300 and 3000 (p<0.0001 for all treatments when compared to MOI 0). In contrast, IL-6 was not secreted by uninfected cells, being significantly increased after infection with Ty21a MOI 300 (p<0.05 compared to MOI 0). However, the highest response was obtained after infection with Ty21a at MOI 3000 (p<0.0001 compared to MOI 0). Our results suggest that Ty21a is able to induce cytokine secretion by murine urothelial cells, which may participate in bladder tumor regression. In the human urothelial cell lines (RT4), both IL-8 and IL-6 were secreted in the supernatant in absence of bacteria. Ty21a infection at MOI 200 or 2000 resulted in higher secretion of both IL-8 and IL-6 (p<0.001 when compared to MOI 0). TNF-α and IL-1β were only induced after "infection" with the higher dose of Ty21a (MOI 2000) (p<0.0001 when compared to MOI 0). RT112 human tumor cells secreted lower amounts of IL-8 and IL-6 than RT4 cell in absence of bacteria. Both cytokines were increased after infection with Ty21a at MOI of 600 or 6000. This suggests that Ty21a promote secretion of different inflammatory cytokines by human cancer cell lines, which may participate in anti-tumor immune response and tumor regression in humans.

REFERENCES

Alexandroff, A. B., Jackson, A. M., O'Donnell, M. A., & James, K. (1999). BCG immunotherapy of bladder cancer: 20 years on. Lancet, 353(9165), 1689-1694. doi: 10.1016/S0140-6736(98)07422-4

Arnold, J., de Boer, E. C., O'Donnell, M. A., Bohle, A., & Brandau, S. (2004). Immunotherapy of experimental bladder cancer with recombinant BCG expressing interferon-gamma. Journal of immunotherapy, 27(2), 116-123.

Askeland, E. J., Newton, M. R., O'Donnell, M. A., & Luo, Y. (2012). Bladder Cancer Immunotherapy: BCG and Beyond. Adv Urol, 2012, 181987. doi: 10.1155/2012/181987

Begier, E. M., Burwen, D. R., Haber, P., Ball, R., & Vaccine Adverse Event Reporting System Working, G. (2004). Postmarketing safety surveillance for typhoid fever vaccines from the Vaccine Adverse Event Reporting System, July 1990 through June 2002. Clin Infect Dis, 38(6), 771-779. doi: 10.1086/381548

Biot, C., Rentsch, C. A., Gsponer, J. R., Birkhauser, F. D., Jusforgues-Saklani, H., Lemaitre, F., . . . Albert, M. L. (2012). Preexisting BCG-specific T cells improve intravesical immunotherapy for bladder cancer. Sci Transl Med, 4(137), 137ra172. doi: 10.1126/scitranslmed.3003586

Black, R. E., Levine, M. M., Ferreccio, C., Clements, M. L., Lanata, C., Rooney, J., & Germanier, R. (1990). Efficacy of one or two doses of Ty21a Salmonella typhi vaccine in enteric-coated capsules in a controlled field trial. Chilean Typhoid Committee. Vaccine, 8(1), 81-84.

Chen, F., Zhang, G., Cao, Y., Hessner, M. J., & See, W. A. (2009). MB49 murine urothelial carcinoma: molecular and phenotypic comparison to human cell lines as a model of the direct tumor response to bacillus Calmette-Guerin. J Urol, 182(6), 2932-2937. doi: 50022-5347(09)02014-X [pii] 10.1016/j.juro.2009.08.018

Chorobik, P., Czaplicki, D., Ossysek, K., & Bereta, J. (2013). Salmonella and cancer: from pathogens to therapeutics. Acta Biochim Pol, 60(3), 285-297.

De Boer, E. C., De Jong, W. H., Van Der Meijden, A. P., Steerenberg, P. A., Witjes, J. A., Vegt, P. D., . . . Ruitenberg, E. J. (1991). Presence of activated lymphocytes in the urine of patients with superficial bladder cancer after intravesical immunotherapy with bacillus Calmette-Guerin. Cancer Immunol Immunother, 33(6), 411-416.

Decrausaz, L., Goncalves, A. R., Domingos-Pereira, S., Pythoud, C., Stehle, J. C., Schiller, J., . . . Nardelli-Haefliger, D. (2011). A novel mucosal orthotopic murine model of human papillomavirus-associated genital cancers. Int J Cancer, 128(9), 2105-2113. doi: 10.1002/ijc.25561

Engels, E. A., Falagas, M. E., Lau, J., & Bennish, M. L. (1998). Typhoid fever vaccines: a meta-analysis of studies on efficacy and toxicity. BMJ, 316(7125), 110-116.

Hayashi, T., Crain, B., Con, M., Chan, M., Cottam, H. B., Maj, R., . . . Carson, D. A. (2010). Intravesical Toll-like receptor 7 agonist R-837: optimization of its formulation in an orthotopic mouse model of bladder cancer. Int J Urol, 17(5), 483-490. doi: IJU2503 [pii] 10.1111/j.1442-2042.2010.02503.x Hegele, A., Dalpke, A., Barth, P., Varga, Z., Heeg, K., Hofmann, R., & Olbert, P. (2004). Antineoplastic effect of immunostimulatory DNA (CpG-ODN) in a murine C57-BL6/MB-49 transitional cell carcinoma model. Anticancer Res, 24(4), 2225-2230.

Hegele, A., Dalpke, A., Heeg, K., Barth, P., Varga, Z., Hofmann, R., & Olbert, P. (2005). Immunostimulatory CpG oligonucleotides reduce tumor burden after intravesical administration in an orthotopic murine bladder cancer model. Tumour Biol, 26(5), 274-280. doi: 10.1159/000087380

Kresowik, T. P., & Griffith, T. S. (2009). Bacillus Calmette-Guerin immunotherapy for urothelial carcinoma of the bladder. Immunotherapy, 1(2), 281-288. doi: 10.2217/1750743X.1.2.281

Levine, M. M., Ferreccio, C., Black, R. E., Tacket, C. O., & Germanier, R. (1989). Progress in vaccines against typhoid fever. Rev Infect Dis, 11 Suppl 3, S552-567.

Levine, M. M., Kaper, J. B., Herrington, D., Ketley, J., Losonsky, G., Tacket, C. O., . . . Cryz, S. (1988). Safety, immunogenicity, and efficacy of recombinant live oral cholera vaccines, CVD 103 and CVD 103-HgR. Lancet, 2(8609), 467-470.

Loskog, A., Ninalga, C., Hedlund, T., Alimohammadi, M., Malmström, P., & Tötterman, T. (2005). Optimization of the MB49 mouse bladder cancer model for adenoviral gene therapy. Lab Anim, 4, 384-393.

Mangsbo, S. M., Nanalga, C., Essand, M., Loskog, A., & Totterman, T. H. (2008). CpG therapy is superior to BCG in an otrhotopic bladder cancer model and generates CD4+ T-cell immunity. J. Immunother., 31, 34-42.

Masters, J. R., Hepburn, P. J., Walker, L., Highman, W. J., Trejdosiewicz, L. K., Povey, S., . . . Franks, L. M. (1986). Tissue culture model of transitional cell carcinoma: characterization of twenty-two human urothelial cell lines. Cancer Res, 46(7), 3630-3636.

Ninalga, C., Loskog, A., Klevenfeldt, M., Essand, M., & Totterman, T. H. (2005). CpG oligonucleotide therapy cures subcutaneous and orthotopic tumors and evokes protective immunity in murine bladder cancer. J Immunother, 28(1), 20-27.

Revaz, V., Debonneville, A., Bobst, M., & Nardelli-Haefliger, D. (2008). Monitoring of vaccine-specific gamma interferon inductionin in genital mucosa of mice by real-time reverse-transcription-PCR. Clin. Vacc. Immunol., 5, 757-764.

Rigby, C. C., & Franks, L. M. (1970). A human tissue culture cell line from a transitional cell tumour of the urinary bladder: growth, chromosome pattern and ultrastructure. Br J Cancer, 24(4), 746-754.

Saban, M. R., Simpson, C., Davis, C., Wallis, G., Knowlton, N., Frank, M. B., . . . Saban, R. (2007). Discriminators of mouse bladder response to intravesical Bacillus Calmette-Guerin (BCG). BMC Immunol, 8, 6. doi: 10.1186/1471-2172-8-6

Seow, S. W., Cai, S., Rahmat, J. N., Bay, B. H., Lee, Y. K., Chan, Y. H., & Mahendran, R. (2010). Lactobacillus rhamnosus GG induces tumor regression in mice bearing orthotopic bladder tumors. Cancer Sci, 101(3), 751-758. doi: CAS1426 [pii] 10.1111/j.1349-7006.2009.01426.x Summerhayes, I. C., & Franks, L. M. (1979). Effects of donor age on neoplastic transformation of adult mouse bladder epithelium in vitro. J Natl Cancer Inst, 62, 1017-1023.

Takahashi, T., Kushiro, A., Nomoto, K., Uchida, K., Morotomi, M., Yokokura, T., & Akaza, H. (2001). Antitumor effects of the intravesical instillation of heat killed cells of the Lactobacillus casei strain Shirota on the murine orthotopic bladder tumor MBT-2. J Urol, 166(6), 2506-2511.

Toso, J. F., Gill, V. J., Hwu, P., Marincola, F. M., Restifo, N. P., Schwartzentruber, D. J., . . . Rosenberg, S. A. (2002). Phase I study of the intravenous administration of attenuated Salmonella typhimurium to patients with metastatic melanoma. J Clin Oncol, 20(1), 142-152.

Vendrell, A., Gravisaco, M. J., Pasetti, M. F., Croci, M., Colombo, L., Rodriguez, C., . . . Waldner, C. I. (2011). A novel *Salmonella Typhi*-based immunotherapy promotes tumor killing via an antitumor Th1-type cellular immune response and neutrophil activation in a mouse model of breast cancer. Vaccine, 29(4), 728-736. doi: 10.1016/j.vaccine.2010.11.017

Wall, D. M., Srikanth, C. V., & McCormick, B. A. (2010). Targeting tumors with *salmonella Typhimurium*-potential for therapy. Oncotarget, 1(8), 721-728.

The invention claimed is:

1. A method of treatment of bladder cancer comprising administering to a subject in need thereof a pharmaceutical composition comprising a live attenuated non-recombinant mutant of *Salmonella enterica* serovar *typhi* strain and/or a non-viable attenuated non-recombinant mutant of *Salmonella enterica* serovar *typhi* strain wherein said viable or non-viable attenuated non-recombinant mutants of *Salmonella enterica* serovar *typhi* strain do not persist in the tumor and are selected from the group consisting of Ty21a, CVD 908-htrA, CVD 909, Ty800, M01ZH09, x9633, x9639, x9640, and x8444 and wherein said pharmaceutical composition is administered locally in the bladder.

2. The method of treatment of claim 1, wherein said pharmaceutical composition is administered locally in the bladder by instillation.

3. The method of treatment of claim 1, wherein said pharmaceutical composition is administered locally in the bladder several times.

4. The method of treatment of claim 1, wherein the bladder cancer is a non-muscle invasive bladder cancer.

5. The method of treatment of claim 1, wherein said pharmaceutical composition further comprises a pharmaceutically acceptable carrier and/or excipient.

6. The method of treatment of claim 1, wherein the treatment reduces the recurrence and/or progression of bladder cancer.

7. The method of treatment of claim 1, wherein the pharmaceutical composition comprising a live attenuated non-recombinant mutant of *Salmonella enterica* serovar *typhi* strain and/or a non-viable attenuated non-recombinant mutant of *Salmonella enterica* serovar *typhi* strain is administered in association with radiotherapy, chemotherapy or immunotherapy, or a combination thereof.

8. A method for inducing apoptosis in a bladder cancer cell, said method comprising administering a pharmaceutical composition comprising a live attenuated non-recombinant mutant of *Salmonella enterica* serovar *typhi* strain and/or a non-viable attenuated non-recombinant mutant of *Salmonella enterica* serovar *typhi* strain wherein said viable or non-viable attenuated non-recombinant mutants of *Salmonella enterica* serovar *typhi* strain are selected from the group consisting of Ty21a, CVD 908-htrA, CVD 909, Ty800, M01ZH09, x9633, x9639, x9640, and x8444 and wherein said pharmaceutical composition is administered locally in the bladder.

* * * * *